US009375388B2

(12) United States Patent
Banerjee

(10) Patent No.: US 9,375,388 B2
(45) Date of Patent: Jun. 28, 2016

(54) NANOPARTICLE BASED COSMETIC COMPOSITION

(71) Applicant: Indian Institute of Technology, Mumbai, Maharashtra (IN)

(72) Inventor: Rinti Banerjee, Mumbai (IN)

(73) Assignee: INDIAN INSTITUTE OF TECHNOLOGY, BOMBAY, Mumbai Maharashtra (IN)

( * ) Notice: Subject to any disclaimer, the term of this patent is extended or adjusted under 35 U.S.C. 154(b) by 53 days.

(21) Appl. No.: 14/346,925

(22) PCT Filed: Sep. 21, 2012

(86) PCT No.: PCT/IN2012/000632
§ 371 (c)(1),
(2) Date: Mar. 24, 2014

(87) PCT Pub. No.: WO2013/072929
PCT Pub. Date: May 23, 2013

(65) Prior Publication Data
US 2015/0224035 A1  Aug. 13, 2015

(30) Foreign Application Priority Data
Sep. 23, 2011  (IN) .......................... 2695/Mum/2011

(51) Int. Cl.
| A61K 8/02 | (2006.01) |
| A61K 8/14 | (2006.01) |
| A61Q 1/02 | (2006.01) |
| A61Q 1/04 | (2006.01) |
| A61Q 1/06 | (2006.01) |
| A61Q 1/10 | (2006.01) |
| A61K 8/67 | (2006.01) |
| A61K 8/19 | (2006.01) |
| A61K 8/20 | (2006.01) |
| A61K 8/23 | (2006.01) |
| A61K 8/26 | (2006.01) |
| A61K 8/36 | (2006.01) |
| A61K 8/55 | (2006.01) |
| A61K 8/92 | (2006.01) |
| A61K 8/97 | (2006.01) |
| A61Q 1/14 | (2006.01) |
| A61Q 19/00 | (2006.01) |

(52) U.S. Cl.
CPC ... *A61K 8/14* (2013.01); *A61K 8/19* (2013.01); *A61K 8/20* (2013.01); *A61K 8/23* (2013.01); *A61K 8/26* (2013.01); *A61K 8/361* (2013.01); *A61K 8/553* (2013.01); *A61K 8/67* (2013.01); *A61K 8/673* (2013.01); *A61K 8/922* (2013.01); *A61K 8/97* (2013.01); *A61Q 1/02* (2013.01); *A61Q 1/04* (2013.01); *A61Q 1/06* (2013.01); *A61Q 1/10* (2013.01); *A61Q 1/14* (2013.01); *A61K 2800/412* (2013.01); *A61K 2800/432* (2013.01); *A61K 2800/82* (2013.01); *A61Q 19/00* (2013.01)

(58) Field of Classification Search
None
See application file for complete search history.

(56) References Cited

U.S. PATENT DOCUMENTS

| 5,496,827 | A | 3/1996 | Patrick |
| 5,654,337 | A | 8/1997 | Roentsch et al. |
| 6,019,990 | A | 2/2000 | Remmereit |
| 6,146,650 | A | 11/2000 | Redlinger |
| 6,432,424 | B1 | 8/2002 | Shapiro et al. |
| 6,464,992 | B2 | 10/2002 | Jacobson et al. |
| 7,776,349 | B2 | 8/2010 | Dechow |
| 2010/0143424 | A1* | 6/2010 | Kanazawa .................. 424/401 |
| 2012/0321683 | A1* | 12/2012 | De La Maza Rivera ................ A61K 9/127 424/401 |

FOREIGN PATENT DOCUMENTS

| CA | 2222061 | 11/1996 |
| DE | 19519273 A1 | 11/1996 |
| DE | 19701651 A1 | 7/1998 |
| DE | 202008014068 U1 * | 9/2009 |
| EP | 0461333 A1 | 12/1991 |
| EP | 1849481 A1 | 10/2007 |
| WO | WO 96/31194 A2 | 10/1996 |
| WO | WO 98/31326 A1 | 7/1998 |
| WO | WO 01/17507 A1 | 3/2001 |
| WO | WO 2010/039490 A2 | 4/2010 |

OTHER PUBLICATIONS

International Search Report for corresponding International Application No. PCT/IN2012/000632 dated Oct. 7, 2014.
Written Opinion for corresponding International Application No. PCT/IN2012/000632 dated Oct. 7, 2014.

* cited by examiner

*Primary Examiner* — Susan Tran
(74) *Attorney, Agent, or Firm* — Vorys, Sater, Seymour and Pease LLP

(57) ABSTRACT

This invention relates to a nanoparticulate composition comprising lipid based nanostructures of 100-200 nm co-encapsulating nutrients selected from the group comprising iron as ferrous, ferric salts or elemental iron, iodine, folic acid, vitamins or micronutrients, incorporated within the matrix of a cosmetic and methods of making said nanoparticle composition.

20 Claims, 6 Drawing Sheets

| Time (h) | FA solution | FA SPC-OA liposomes (4mg/ml) |
|---|---|---|
| 2 | 0 | 3.18 ± 0.54 |
| 4 | 0 | 5.08 ±0.53 |
| 6 | 0 | 20.34 ± 5.48 |
| 8 | 2.39 ± 1.98 | 23.31 ±3.75 |
| 12 | 3.98 ± 3.29 | 45.18 ±8.03 |
| 24 | 5.15± 2.86 | 67.49±11.57 |
| Retention in skin | 20.48±28.97 | 0 |

NANOPARTICLE BASED COSMETIC COMPOSITION

FIELD OF THE INVENTION

The present invention relates to a lipid based cosmetic and dermatological nanoparticulate composition of multiple nutrients such as iron, iodine and folic acid combined along with biocompatible amphiphilic lipids and nanostructured carriers for mitigating nutritional deficiencies.

BACKGROUND OF THE INVENTION

Nutrient deficiencies lead to many health hazards ranging from anemia to mental retardation and neural tube defects. Iron deficiency is particularly common in women of child bearing age and from lower socioeconomic strata. Supplementation in the form of ferrous sulphate is often unacceptable due to cultural barriers, gastric irritation, metallic tastes and other complications. Iodine is another nutrient that requires fortification to prevent life threatening complications due to its deficiency. Another important nutrient is folic acid. Folic acid deficiencies in pregnant women can lead to neural tube defects in newborns.

There is a need for fortification technologies that can ensure optimal intake of these nutrients that is non-invasive and easily acceptable for widespread deployment amongst women in developing countries and from lower socioeconomic strata. All fortification strategies need to keep in mind the local cultures and beliefs for success. Since oral fortification of foods usually requires the need to be tailor-made for local food habits and requires training for successful implementation, there is a need to develop other means of functional preparations that will both alleviate such nutritional deficiencies and also meet consumer acceptance and affordability from all segments of the society.

Consumers, particularly women are always interested in improving the appearance of, for example their skin, lips, hair by imparting to these biological surfaces cosmetic compositions such as face powders, foundations, eyeliners, lip gloss, lipsticks, mascaras, mehendi powder etc to enhance the aesthetic appeal and improve their overall appearance. Thus, cosmetics in the form of skin decorations, (pastes, mehendi, patches and bindis) and eye decorations (kajal, kohl) are commonly used by women worldwide including women from rural areas and developing countries. Therefore, targeting cosmetics that are usually applied transdermally is an attractive option for affording optimal amount of nutrients to the skin. The present invention is directed at nanoparticle based cosmetic compositions that can play a dual role of both imparting an aesthetic appeal to the skin, however, simultaneously revitalizing and affording the vital nutrients to the body.

The stratum corneum is one of the main barriers for getting across the actives through the skin. Technologies that can penetrate through the stratum corneum barrier have the potential to be absorbed by the skin. There are no technologies at present that can afford multiple nutrients like iron, iodine and folic acid through cosmetics like skin and eye decorations.

U.S. Pat. No. 6,432,424 teaches a cosmetic composition comprising carnitine or a cosmetically acceptable salt or ester, pyruvic acid or a cosmetically acceptable salt or ester, a nutrient selected from the group consisting of vitamins or a cosmetically acceptable salt or ester, essential amino acids or a cosmetically acceptable salt or ester, and essential fatty acids, and (iv) trehalose or a cosmetically acceptable salt or ester. The nutrient is selected from the group consisting of vitamin A, vitamin C, vitamin E, an essential amino acid and a cosmetically acceptable salt or ester thereof. The patent does not have any strategies for improved systemic penetration of the nutrients, is limited to certain types of nutrients and does not have any liposomal or nanoparticulate carriers for sustained release of the nutrients and does not deal with the nanoparticulate compositions as envisaged in the present invention U.S. Pat. No. 5,496,827 describes a composition having therapeutic and cosmetic effects having methyl nicotinate in a diluent to increase circulation in the area of application and as a pain reliever and muscle relaxant. The composition may also contain various vitamins, minerals and other nutrients. The methyl nicotinate also acts as a facilitator to promote the transdermal penetration of the vitamins, minerals and other nutrients into the skin. The patent describes the use of methyl nicotinate which may have undesirable side effects. It does not have any liposomal or nanoparticulate carriers and the composition is different from the nanoparticle based cosmetic composition envisaged in the present invention.

U.S. Pat. No. 6,019,990 teaches cosmetic formulations containing free and derivatized forms of conjugated linoleic acid. Certain vitamin/conjugated linoleic acid combinational molecules are described which deliver equimolar amounts of both free components to the epidermis. The patent is limited to specific linoleic acid derived nutrients. The nutrients are delivered only to the epidermis and there are no strategies for the penetration of the nutrients through the full thickness of skin for systemic delivery. It does not have any liposomal or nanoparticulate carriers as present in the nanoparticle based cosmetic composition of the instant invention.

U.S. Pat. No. 6,464,992 involves methods and compositions for delivering micronutrients by formulating them in the form of esters which are convertible to the active form of the micronutrient, for example as a co-ester that inhibits esterases prior to delivery to the cells. The patent does not describe penetrating or fluidising strategies for penetration through the stratum corneum and through the dermis for systemic delivery through the skin. The strategy requires a chemical modification of the nutrient and hence is restricted in its applicability. It does not have any liposomal or nanoparticulate carriers as present in the nanoparticle based cosmetic composition of the instant invention.

U.S. Pat. No. 7,776,349 describes the local delivery of cosmetic and/or pharmaceutical agents locally into the skin or nails. The composition comprises two biocompatible organic solvents, 6 to 30% by weight of lecithin, 0.5 to 19% by weight of at least one or more surfactant one of which are docusates, 40 to 65% by weight of water, 1 to 15% by weight of urea and 0.05 to 5% by weight of thickener like polyethylene glycol, methyl cellulose, and carbomer, and the organic solvents comprise 2 to 30% of isopropyl myristate and 0.5 to 20% of propylene glycol. The drugs delivered are vasodilating agents or antimicrobial agents. The patent deals with the local delivery of specific drugs into the skin and does not deal with the nanoparticle based compositions as envisaged in the present invention that can afford absorption of multiple nutrients through the skin. Many synthetic polymers and organic solvents are involved in the invention which can lead to toxic side effects. There are no specific skin penetrating strategies and does not deal with liposomes or nanoparticles for sustained release of nutrients as can be achieved with the present invention.

Similarly U.S. Pat. No. 5,654,337 describes the delivery of a pharmaceutically active substance like analgesic, anti-inflammatory drugs, a biologically active protein, a cellulite reducer, a substance P antagonist, or an antineoplastic compound, through the skin using a composition consisting of organic solvent like isopropyl myristate and isopropyl palmitate, a polar lipid namely lecithin, a surfactant from the group consisting of docusate sodium, docusate sodium benzoate, docusate calcium, tween 80, polysorbate 80, and ibuprofen, water, and 5 to 20 wt % of urea. The invention does not describe the delivery of multiple nutrients and does not deal with liposomes or nanoparticles for the sustained release of nutrients. The invention contains undesirable organic solvents and urea which can have side effects limiting its applicability.

Thus in view of the foregoing, realizing the need to circumvent the aforementioned drawbacks the inventors of the present invention have endeavored to develop a liposomes or nanoparticle based cosmetic compositions employing biodegradable lipid nanocarriers for fluidization of the stratum corneum that can afford penetration of multiple nutrients through the skin. The present invention avoids the employment of synthetic polymers and organic solvents.

It is therefore an object of the present invention to develop a composition that permits penetration of multiple nutrients through the skin along with commonly used cosmetics. The present invention affords sustained release of nutrients using nanosized carriers.

SUMMARY OF THE INVENTION

It is an object of the present invention to provide a composition of multiple nutrients like iron, iodine and folic acid which are combined along with biocompatible amphiphilic lipids which act as penetration enhancers and nanostructured carriers which allow penetration through the full thickness of the skin and systemically through the capillaries and also allow sustained release of the nutrients over few hours to days. The nutrient loaded nanostructures are entrapped within the matrix of commonly used cosmetics comprising of mehendi powder, water, carbon, lip gloss and the like.

The invention employs multiple strategies of 1) increased fluidization of the stratum corneum lipid layer 2) increased penetration through the layers of the skin due to nanosize 3) penetration through the shafts of hair follicles and 4) sustained release from nanosized carriers for delivery of the nutrients through the skin.

It is another object of the present invention to provide a method of making the nanoparticle composition.

Other features and advantages of the present invention will become apparent as the following detailed description proceeds or may be learned by practice of the invention. It is to be understood that both the foregoing general description and the following detailed description are exemplary and explanatory only and are not restrictive of the invention.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
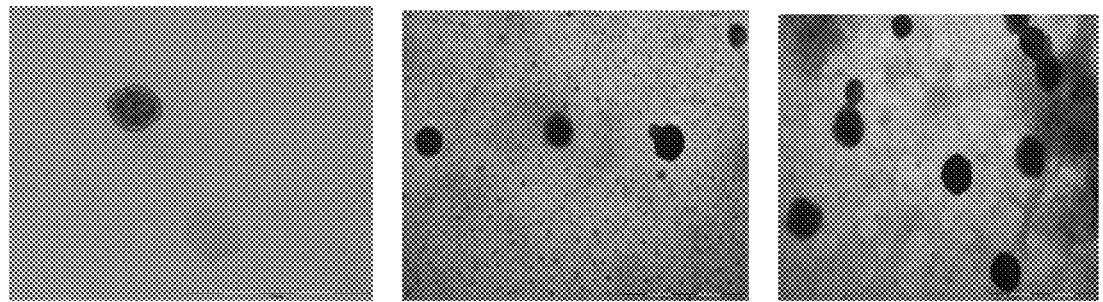
FIG. 1. TEM image of FA SPC-OA liposomes with lipid concentration 4 mg/ml

In describing the invention, the following terminology will be used in accordance with the definitions set forth below. Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described herein. As used herein, each of the following terms has the meaning associated with it in this section. Specific and preferred values listed below for individual components, substituents, and ranges are for illustration only; they do not exclude other defined values or other values within defined ranges for the components and substituents.

The term "nanoparticle" as used herein refers to a nanometer-sized particle, having a diameter of between about 1 nanometer to about 999 nanometers typically having dimensions of less than 250 nanometers. The size distribution of the nanoparticles may be in the range of from 100 nm to 200 nm.

Preferably, the nanostructures employed in the composition are 100-200 nm in diameter which allow penetration through the deep layers of the skin and into the capillaries for systemic absorption.

The nanostructures for nutrient delivery comprise one or more of the following structures namely liposomes, solid lipid nanoparticles, cochleates, nanosized oil droplets and the like.

The term liposome, as used herein, is intended to include any lipid bilayer structure consisting of closed concentric lamellae which enclose one or more aqueous-containing compartments. More specifically, the term "liposome" refers to vesicles surrounded by a bilayer formed of components usually including lipids optionally in combination with non-lipidic components.

In context of the present invention, "nanocochleates" are cylindrical (cigar-like) microstructures that consist of a series of lipid bilayers which are formed as a result of the condensation of small unilamellar negatively charged liposomes. They have a unique multilayered structure consisting of a solid, lipid bilayer sheet rolled up in a spiral or in stacked sheets, with little or no internal aqueous space.

The biological surface may be any surface to which cosmetics, personal care products, and dermatological compositions can be topically applied, including but not limited to skin, hair, the inventive composition having the characteristics and properties described herein, in an amount effective to afford penetration through the full thickness of the skin.

The composition embraced by the present invention can be provided in any cosmetically and/or dermatologically suitable form, including but not limited to a cream, a wax-stick, lotion, balm, gloss and the like. In addition, the composition contemplated by this invention can include one or more compatible cosmetically acceptable adjuvants as used and known by the skilled practitioner.

The present invention provides a cosmetic composition that comprises the nutrient loaded nanoparticles in an amount of 0.0001 to 99.9% by weight based on the total weight of the composition.

The lipids used in the composition consist of one or more of the following soya phosphatidylcholine, egg lecithin, fatty acids, coconut oil, soya bean oil, peanut oil, mustard oil, essential aromatic oils.

The nutrients loaded within the invention include two or more of the following nutrients namely iron (as ferrous or ferric salts or as elemental iron), iodine and folic acid and in addition may include other vitamins and micronutrients. The nutrients are loaded on the surface or within the matrix or both of the nano structures.

The invention is stable on storage and does not leach out any breakdown products on storage at room temperature over a period of a month The invention does not involve the use of any synthetic polymers or synthetic surfactants or urea or nicotinates to stabilise or improve penetration of the nutrients.

The invention may optionally contain biodegradable biocompatible biopolymers like gellan, xanthan, alginate, starch, chitosan which may form surface coatings of the nanostructures or may be chemically linked to the surface of the nanostructures using ethyldicarbodimide linkages.

The invention uses multiple strategies of 1) increased fluidisation of the stratum corneum lipid layer 2) increased penetration through the layers of the skin due to nanosize 3) penetration through the shafts of hair follicles and 4) sustained release from nanosized carriers for delivery of the nutrients through the skin.

On application to the surface of skin in the form of pastes and patches, the nutrients are delivered systemically and are detectable in the plasma making them suitable for fortification and prevention of nutritional deficiencies.

It should be understood that the foregoing description is only illustrative of the present invention. Various alternatives and modifications can be devised by those skilled in the art without departing from the invention. Accordingly, the present invention is intended to embrace all such alternatives, modifications and variations that fall within the scope of the description above.

Example 1

Preparation of Liposomes

Liposomes of folic acid (FA) were prepared by the thin film hydration method. Briefly lipids, soya phosphatidylcholine: oleic acid SPC:OA in mass ratio of 9:1 (w/w) was dissolved in methanol/chloroform (1:2 v/v) in a round bottom flask, and was dried to a thin lipid film in a rotary evaporator at 40° C. under vacuum. The dry film was hydrated with fresh solution of folic acid in phosphate buffer saline (2 mg/ml, pH 7.4) in a rotary evaporator at 45° C. for 1 h with a rotation speed of 150 rpm to form multi-lamellar vesicles. The final lipid concentration was 4 mg/ml. The suspension was centrifuged at 25000 g, 4° C. for 45 minutes and the pellet was reconstituted in supernatant to achieve final concentration of lipid as 20 mg/ml. The resultant liposomal suspension was sonicated for two cycles of 1 min period with 1 s on, 1 s off intervals at 30% amplitude interrupted by a 2 min resting period at 25° C. using a probe sonicator resulting in a translucent aqueous dispersion of small unilamellar vesicles (SUVs). The cosmetics are prepared by incorporation of these nanosized liposomes.

Example 2

The particle size distribution of folic acid loaded liposomes was determined after appropriate dilution of the liposomal dispersion with saline and reading carried out at 90° with respect to the incident beam by dynamic laser scattering (DLS) using laser particle analyzer at 25° C. Folic acid liposomes of 170 to 300 nm were prepared. The nanosized vesicles are incorporated within cosmetics.

TABLE 1

Effect of increasing lipid concentration on encapsulation efficiency and particle size of liposomes.

| Lipid concentration (mg/mL) | Encapsulation Efficiency (%) | Particle size (nm) |
| --- | --- | --- |
| 4 | 10 ± 1.606 | 170 ± 4.05 |
| 12 | 70.1 ± 0.332 | 297.1 ± 0.246 |
| 16 | 40.2 ± 0.481 | 292.0 ± 0.399 |
| 20 | 5.9 ± 0.255 | 295.6 ± 0.380 |

The TEM images of folic acid liposomes as shown in FIG. 1 displayed uniform unilamellar liposomes of size approximately 100-150 nm.

Example 3

Confocal Laser Scanning Microscopy

Figure 2:
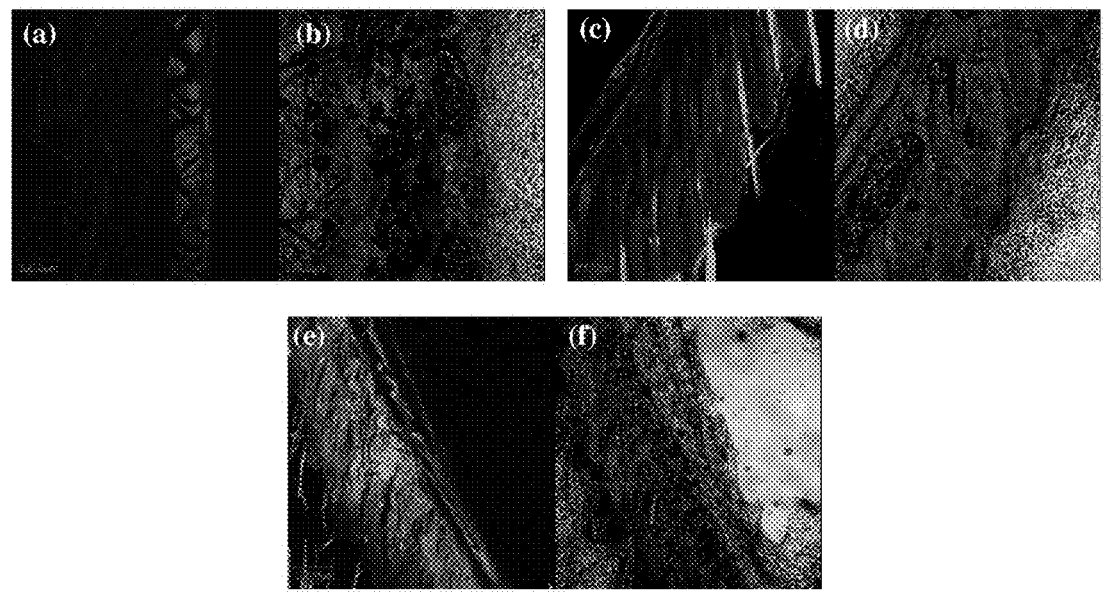
FIG. 2. CLSM image of rat skin: without calcein dye under (a) calcein filter (b) bright field; with free calcein solution under (c) calcein filter (d) bright field; with calcein-loaded SPC liposomes under (e) calcein filter (f) bright field.
Figure 3:
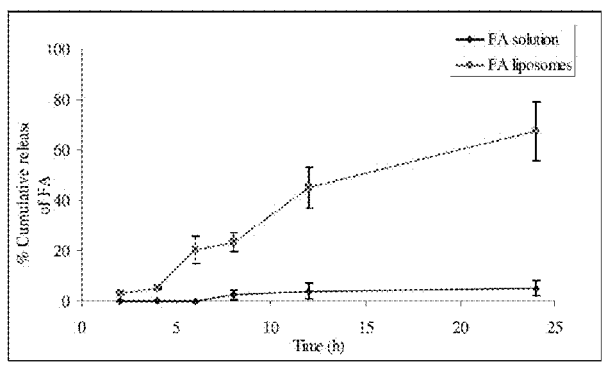
FIG. 3. In vitro time course of cumulative permeation of folic acid from (■) FA SPC-OA liposomes (lipid concentration 4 mg/ml) (♦) FA solution 24 h after their application on rat skin (Mean±Standard error)
Figure 4:
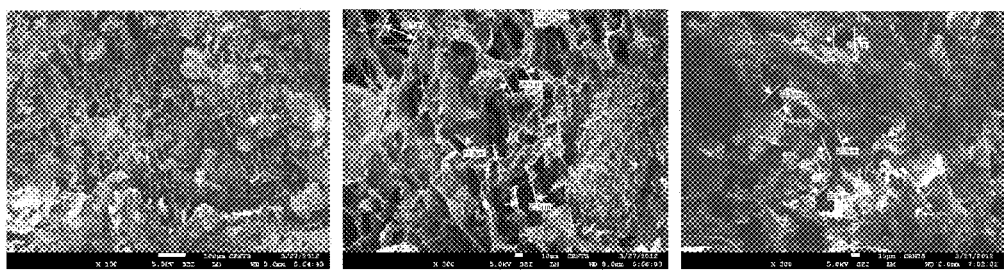
FIG. 4 SEM images of FA SPC-OA Lipogel in mehendi.
Figure 5:
FIG. 5. Folic acid loaded SPC-OA liposomes (4 mg/ml) loaded in mehendi

The penetration of dye loaded liposomes through skin showed enhanced permeation compared to free dye. The images show that the free dye is visible only at the surface of the skin and around the hair follicles, dye from the liposomes penetrate into the upper layers of skin, fluorescence is visible even in deeper layers of the skin (FIG. 2).

Example 4

The permeation of folic acid from nanovesicles of folic acid, soya phosphatidylcholine and oleic acid showed a significant improvement over that of free solution. The presence of 100-150 nm soyaphosphatidylcholine-oleic acid loaded liposomes containing folic acid enhanced the permeation of folic acid through skin.

TABLE 2

Flux and Permeation coefficients of FA solution and FA SPC-OA liposomes treated with rat skin

| Formulation | Flux (µg/(cm$^2$h)) | Permeability coefficient (cm/h) |
|---|---|---|
| FA solution | 0.484 ± 0.302 | 0.002 ± 0.001 |
| FA SPC-OA liposomes | 13.09 ± 3.264 | 0.065 ± 0.016 |

Example 5

Soya phosphatidylcholine and Eugenol/Eucalyptus oil were dissolved in mass ratio (7:3) in methanol/chloroform (1:2 v/v). The dry film was hydrated with fresh solution of folic acid in phosphate buffer saline (2 mg/ml, pH 7.4) in a rotary evaporator at 45° C. for 1 h with a rotation speed of 150 rpm to form multi-lamellar vesicles. The final concentration lipid concentration was maintained at 4 mg/ml. The resultant liposomal suspension was sonicated for two cycles of 1 min period with 1 s on, 1 s off intervals at 30% amplitude interrupted by a 2 min resting period at 25° C. using a probe sonicator resulting in a translucent aqueous dispersion of small unilamellar vesicles (SUVs). The suspension was centrifuged at 25000 g, 4° C. for 45 minutes and the pellet was reconstituted in supernatant to achieve final concentration of lipid as 20 mg/ml.

TABLE 3

Physicochemical parameters for various formulations with varying penetration enhancers

| | Particle size (nm) | Polydispersity Index | Zeta Potential (mV) |
|---|---|---|---|
| SPC: Eugenol | 189.13 | 0.195 | −13.15 ± 1.68 |
| SPC: *Eucalyptus* | 212.2 | 0.273 | −11.53 ± 7.37 |

Example 6

Preparation of Liposome Loaded in Gellan Gum (Lipogel)

Dry gellan gum powder was dispersed in distilled water maintained at 70° C. The dispersion was stirred at 70° C. for 20 min using a magnetic stirrer to facilitate hydration of gellan gum and continued till gellan is completely dissolved. After complete dissolution of gellan gum, the mixture was allowed to cool. On attaining 40° C., concentrated FA liposomes of soya phosphatidylcholine and oleic acid were added to the gellan gum solution with continuous stirring and volume was made up such that concentration of gellan gum was 0.3% w/v. The solution was further allowed to cool to room temperature (25±5° C.) to form gel. Liposomes in gel was then incorporated within the cosmetic (mehendi/sindoor/alta/multani mitti)

Example 7

Preparation of FA SPC-OA Liposomes Loaded Mehendi

Appropriate quantity of mehendi powder was dispersed in distilled water under constant stirring with a glass rod, taking care to avoid the formation of indispersible lumps. Folic acid loaded SPC-OA liposomes or liposomes in gellan gel into this mehendi paste by physical mixing or blending. The mehendi samples loaded with folic acid containing nanovesicles were stable on storage.

Example 8

Preparation of FA SPC-OA Liposomes Loaded Sindoor

Figure 6:
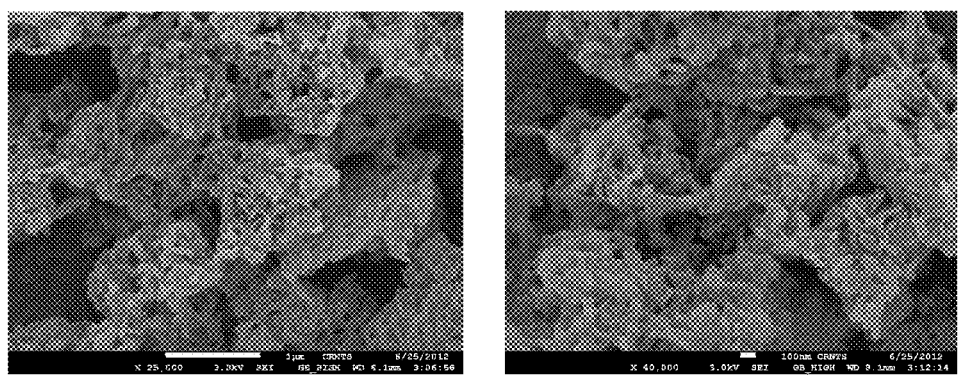
FIG. 6. SEM image of FA SPC-OA liposomes loaded in liquid sindoor
Figure 7:
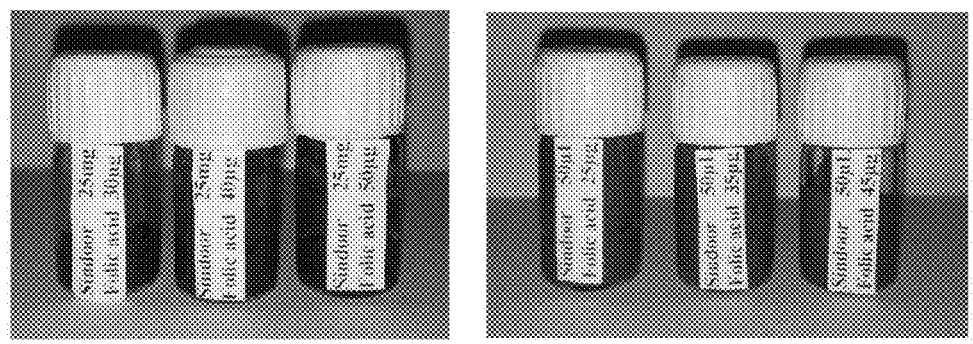
FIG. 7. Folic acid loaded SPC-OA liposomes (4 mg/ml) loaded in (a) powder sindoor (b) liquid sindoor.

Powdered Sindoor loaded with FA SPC-OA liposomes were prepared by incorporation of FA SPC-OA liposomes into Sindoor by physical mixing taking care to avoid the formation of indispersible lumps till formation of spreadable paste. For liposome loaded liquid sindoor, appropriate quantity of liquid Sindoor was mixed with FA SPC-OA liposomes by simple vortex mixing. Sindoor is made with turmeric and alum or lime, or grounded saffron however modern Sindoor mainly uses vermilion, which is an orange-red pigment. Sindoor is a traditional red or orange-red colored cosmetic powder from India, worn by married women along the parting of their hair indicating their marital status. The surface morphology of folic acid loaded soya phosphatidylcholine-oleic acid nanovesicles incorporated in Sindoor is displayed in FIG. 6. The stable suspension of soya phosphatidylcholine-oleic acid loaded liposomes within sindoor are seen in FIG. 7.

Example 10

Preparation of FA SPC-OA Liposomes Loaded Sindoor

Figure 8:
FIG. 8. Folic acid loaded SPC-OA liposomes (4 mg/ml) loaded in liquid alta

Alta is a scarlet red stain of cosmetic traditionally made of the betel leaf, or 'paan' and used by women in north and northeastern parts of India to decorate their feet and palms (usually in various shades of red) and with medicinal properties. Commercially red lac, a resinous substance exuded by the *Laccifer lacca* is used. Powdered Alta loaded with FA SPC-OA liposomes was prepared by incorporation of FA SPC-OA liposomes into Alta by physical mixing taking care to avoid the formation of indispersible lumps till formation of spreadable paste. Appropriate quantity of liquid Alta was mixed with FA SPC-OA liposomes by simple vortex mixing. The stable folic acid loaded soya phosphatidylcholine oleic acid liposomes within multani mitti is shown in FIG. 8.

Example 11

Preparation of FA SPC-OA Liposomes Loaded Multani Mitti

Figure 9:
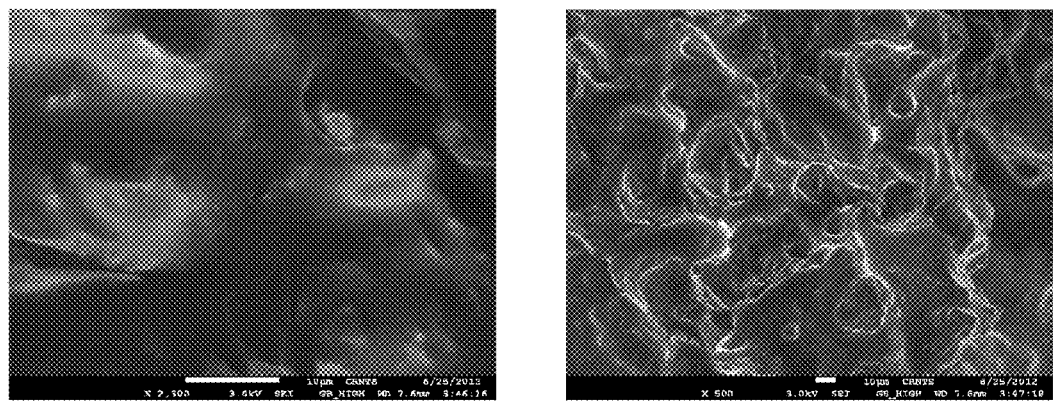
FIG. 9. SEM images of multani mitti loaded FA SPC-OA liposomes
Figure 10:
FIG. 10. Folic acid loaded SPC-OA liposomes (4 mg/ml) loaded in multani mitti
Figure 11:
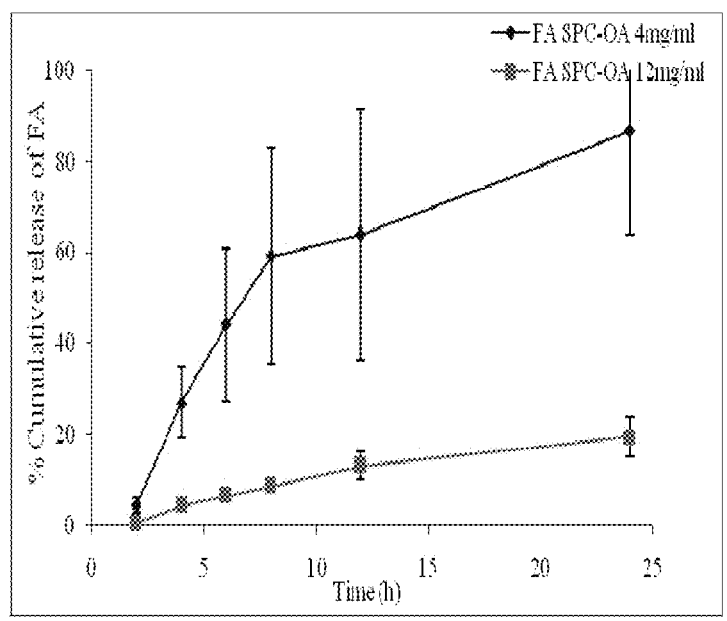
FIG. 11 Penetration of folic acid through skin using soya phosphatidylcholine-oleic acid nanovesicles within mehendi at concentrations of 4 and 12 mg/ml

Powdered Multani mitti, or Fuller's earth loaded with FA SPC-OA liposomes were prepared by incorporation of FA SPC-OA liposomes into multani mitti by physical mixing taking care to avoid the formation of indispersible lumps till formation of easy to spread paste. SEM image pf multani mitti loaded with FA SPC-OA liposomes is depicted in FIG. 9. Multani mitti loaded FA SPC-OA liposomes were found to be stable on storage

Example 12

The folic acid loaded soya phosphatidylcholine-oleic acid liposomes within mehendi showed enhanced penetration (86%) of folic acid through skin over 24 hours

The invention claimed is:

1. A nanoparticulate composition comprising lipid based nanostructures made up of soya phosphatidylcholine and at least one member selected from the group consisting of oleic acid, eugenol, *eucalyptus* oil, menthol and other oils;
wherein said nanostructures have a size of 100-200 nm and co-encapsulate at least one nutrient selected from the group consisting of iron as ferrous, ferric salts or elemental iron, iodine, folic acid, vitamins and micronutrients, incorporated within a matrix of a cosmetic.

2. The nanoparticulate composition as claimed in claim 1, wherein the nanostructure is selected from one or more members of the group consisting of liposomes, solid lipid nanoparticles, nanovesicles, nanocochleates, and nanosized oil droplets.

3. The nanoparticulate composition as claimed in claim 1, wherein the nanostructure is a nanovesicle.

4. The nanoparticulate composition as claimed in claim 3, wherein the nanovesicles are made of soya phosphatidylcholine and oleic acid in a 9:1 wt/wt ratio.

5. The nanoparticle composition as claimed in claim 3, wherein the nanovesicles are made of soya phosphatidylcholine along with at least one member of the group consisting of eugenol, *eucalyptus* oil, menthol and other oils.

6. The nanoparticle composition as claimed in claim 5, wherein the cosmetics are selected from the group consisting of mehendi, sindoor, alta, multani mitti, and lip stick.

7. A method of making a nanoparticle composition comprising lipid based nanostructures having a size of 100-200 nm co-encapsulating nutrients incorporated within a matrix of a cosmetic said method comprising the steps of:
a. Dissolving soya phosphatidylcholine:oleic acid SPC:OA in mass ratio of 9:1 (w/w) in methanol/chloroform (1:2 v/v) to form a mixture,
b. A thin lipid film is formed by drying the mixture of step (a) in a rotary evaporator at 40° C. under vacuum,
c. The film was hydrated with fresh solution of folic acid or iron salt in phosphate buffer saline to form a liposomal suspension,
d. The suspension of step (c) was centrifuged at 25000 g, 4° C. for 45 minutes to obtain a pellet, and the pellet was reconstituted in supernatant to achieve the liposomal suspension having final concentration of lipid as 20 mg/ml,
e. Sonication of the liposomal suspension to form a translucent aqueous dispersion of small unilamellar vesicles (SUVs), and
f. Careful mixing at room temperature of the SUVs of step (e) within a base of the cosmetic.

8. A method of making a nanoparticle composition comprising lipid based nanostructures of having a size 100-200 nm co-encapsulating nutrients incorporated within a matrix of a cosmetic said method comprising the steps of:
a) Dissolving either soya phosphatidylcholine and Eugenol in mass ratio (7:3) or soya phosphatidylcholine and *Eucalyptus* oil in mass ratio (7:3) in methanol/chloroform (1:2 v/v) to form a mixture,
b) A thin lipid film is formed by drying the mixture of step (a) in a rotary evaporator at 45° C. under vacuum,
c) The film was hydrated with fresh solution of folic acid in phosphate buffer saline to form a liposomal suspension,
d) Sonication of the liposomal suspension of step (c) to form a translucent aqueous dispersion of small unilamellar vesicles (SUVs),
e) The dispersion of step (d) containing the SUVs was centrifuged at 25000 g, 4° C. for 45 minutes to obtain a pellet containing the SUVs, and the pellet was reconstituted in supernatant to achieve a reconstituted mixture containing the SUVs having a final concentration of lipid as 20 mg/ml, and
f) Careful mixing at room temperature of the SUVs of step (e) within a base of the cosmetic.

9. A cosmetic incorporating within its matrix a nanoparticle as claimed in claim 1.

10. The nanoparticulate composition as prepared from the method claimed in claim 8, wherein the nanoparticle composition is incorporated into cosmetics.

11. The nanoparticulate composition as prepared from the method claimed in claim 7, wherein the nanoparticle composition is incorporated into cosmetics and causes penetration of the nutrient through layers of skin of a user after application to the skin.

12. A nanoparticulate composition comprising lipid based nanostructures made up of one or more lipids selected from the group consisting of soya phosphatidylcholine, egg lecithin, fatty acids, coconut oil, soya bean oil, peanut oil, and mustard oil, and at least one member selected from the group consisting of oleic acid, eugenol, *eucalyptus* oil, menthol and other oils;
wherein said nanostructures have a size of 100-200 nm and co-encapsulate at least one nutrient selected from the group consisting of iron as ferrous, ferric salts or elemental iron, iodine, folic acid, vitamins and micronutrients, incorporated within a matrix of a cosmetic.

13. The nanoparticle composition as claimed in claim 3, wherein the nanovesicles comprise at least one member of the group consisting of eugenol, *eucalyptus* oil, and menthol.

14. The nanoparticle composition as claimed in claim 5, wherein the cosmetics are selected from the group consisting of mehendi, sindoor, alta, and multani mitti.

15. The nanoparticle composition as claimed in claim 5, wherein the cosmetic is multani mitti.

16. The nanoparticle composition as claimed in claim 1, further comprising a biocompatible biopolymer selected from the group consisting of gellan, xanthan, alginate, starch, and chitosan which may form surface coatings of the nanostructures or may be chemically linked to the surface of the nanostructures using ethyldicarbodimide linkages.

17. The nanoparticulate composition as claimed in claim 3, wherein the nanovesicles are either made of soya phosphatidylcholine and Eugenol in a 7:3 wt/wt ratio or made of soya phosphatidylcholine and *Eucalyptus* oil in a 7:3 wt/wt ratio.

18. The nanoparticulate composition as claimed in claim 1, wherein the nanostructure is selected from one or more members of the group consisting of nanocochleates and nanosized oil droplets.

19. The nanoparticle composition as claimed in claim 1, consisting of said lipid based nanostructures made up of soya phosphatidylcholine and at least one member selected from the group consisting of oleic acid, eugenol, *eucalyptus* oil, menthol or other oils; wherein said nanostructures have a size of 100-200 nm and co-encapsulate at least one nutrient selected from the group consisting of iron as ferrous, ferric salts or elemental iron, iodine, folic acid, vitamins and micronutrients, incorporated within the matrix of a cosmetic.

20. A method of penetrating at least one nutrient selected from the group consisting of iron as ferrous, ferric salts or elemental iron, iodine, folic acid, vitamins or micronutrients into skin of a user, comprising applying the composition of claim 1 to said skin.

* * * * *